(12) United States Patent
Tseng et al.

(10) Patent No.: US 8,785,136 B2
(45) Date of Patent: Jul. 22, 2014

(54) IMMUNODETECTION PROBE AND METHOD OF IMMUNODETECTION USING THE SAME

(75) Inventors: Fan Gang Tseng, Hsinchu (TW); Yuan Tai Tseng, Nantou County (TW)

(73) Assignee: National Tsing Hua University, Hsinchu (TW)

( * ) Notice: Subject to any disclaimer, the term of this patent is extended or adjusted under 35 U.S.C. 154(b) by 859 days.

(21) Appl. No.: 12/917,706

(22) Filed: Nov. 2, 2010

(65) Prior Publication Data

US 2011/0136132 A1 Jun. 9, 2011

(30) Foreign Application Priority Data

Dec. 9, 2009 (TW) ................................ 98142002 A

(51) Int. Cl.
| | | |
|---|---|---|
| *G01N 33/53* | (2006.01) | |
| *A61B 5/00* | (2006.01) | |
| *A61B 5/145* | (2006.01) | |
| *A61B 5/1459* | (2006.01) | |

(52) U.S. Cl.
CPC ........... *A61B 5/14546* (2013.01); *A61B 5/6848* (2013.01); *A61B 5/14528* (2013.01); *A61B 5/1459* (2013.01)
USPC .......................................................... 435/7.1

(58) Field of Classification Search
None
See application file for complete search history.

(56) References Cited

U.S. PATENT DOCUMENTS

| | | | | |
|---|---|---|---|---|
| 4,344,438 | A * | 8/1982 | Schultz .......................... | 600/341 |
| 5,127,077 | A * | 6/1992 | Iyer et al. ...................... | 385/116 |
| 6,122,536 | A * | 9/2000 | Sun et al. ...................... | 600/341 |
| 6,584,335 | B1 * | 6/2003 | Haar et al. .................... | 600/322 |
| 6,627,177 | B2 * | 9/2003 | Singaram et al. .............. | 424/9.6 |
| 6,750,311 | B1 * | 6/2004 | Van Antwerp et al. ......... | 528/77 |
| 7,146,203 | B2 * | 12/2006 | Botvinick et al. ............. | 600/345 |
| 8,275,436 | B2 * | 9/2012 | Wang et al. ................... | 600/324 |
| 8,383,047 | B2 * | 2/2013 | Obeid et al. ............... | 422/82.06 |
| 2008/0144039 | A1 | 6/2008 | Tan et al. | |
| 2008/0200788 | A1 * | 8/2008 | Brister et al. ................. | 600/345 |
| 2012/0046642 | A1 * | 2/2012 | Soykan et al. ................ | 604/503 |

OTHER PUBLICATIONS

Office Action of TW counterpart application No. 098142002 dated Sep. 27, 2012 cites US 2008/0144039, D.J. Monk et al., "Optical Fiber-based Biosensors", and R.R. Sathuluri et al., "Microsystems Technology and Biosensing".
English Abstract of Office Action of TW counterpart application No. 098142002 dated Sep. 27, 2012.
D.J. Monk et al., "Optical Fiber-based Biosensors", Anal Bioanal Chem, 2004, p. 931-945, vol. 379.
R.R. Sathuluri et al., "Microsystems Technology and Biosensing", Adv. Biochen. Engin/Biotechnol, Nov. 13, 2007, p. 285-350, vol. 109.

* cited by examiner

*Primary Examiner* — Ann Lam
(74) *Attorney, Agent, or Firm* — Muncy, Geissler, Olds & Lowe, P.C.

(57) ABSTRACT

An immunodetection probe comprises a needle structure having a compartment and configured to be inserted into an organic tissue, a dialysis membrane configured to isolate the compartment from the organic tissue, a detection device having a detection portion and a plurality of receptors, a first optical fiber coupled to the needle structure, and a pair of tubes connected to the compartment. The plurality of receptors are disposed on an end surface of the detection portion for conjugating target antibodies, wherein the detection portion is disposed in the compartment. The first optical fiber is configured to introduce light incident on photo-induced molecules adjacent to the end surface of the detection portion so as to cause a change in the pH level of the solution adjacent to the end surface of the detection portion. The pair of tubes is configured to transport the solution containing the photo-induced molecules into the compartment.

24 Claims, 6 Drawing Sheets

IMMUNODETECTION PROBE AND METHOD OF IMMUNODETECTION USING THE SAME

BACKGROUND OF THE INVENTION (A) Field of the Invention

The present invention relates to an immunodetection probe and a method of immunodetection using the same.

(B) Description of the Related Art

The main method for detecting molecules such as proteins or enzymes in biomedical systems is to use a micro-dialysis probe for sampling a biological specimen. Subsequently, the specimen collected from dialysis fluid is sampled and detected by enzyme-linked immunoassay (ELISA) for determining the existence of a target, or detecting a quantity of the target. Although such method provides a high level of sensitivity, an extended multi-hour sampling period is required, and thus the efficiency is poor.

In order to resolve the problem of inefficiency, various biosensors have been developed over the years and a fiber optic surface plasma resonance (SPR) biosensor has become one of the promising alternatives among the biosensors. However, the fiber optic SPR biosensor requires a sensing area with a width of at least 5 mm, and such required sensing area cannot be further reduced. Moreover, once target molecules are conjugated in the sensing area, the fiber needs to be replaced. Subjects will feel uncomfortable due to such frequent replacement of the fibers.

Accordingly, based on the drawback of the method for detecting molecules such as proteins or enzymes, as mentioned above, there is a need to provide a detection apparatus and method for detecting molecules such as proteins or enzymes.

SUMMARY OF THE INVENTION

The objective of the present invention is to provide an immunodetection probe which combines a detection function and a reusable mechanism, and thus continuous in-situ detection can be performed.

According to an aspect of the present invention, the immunodetection probe comprises a needle structure, a dialysis membrane, a detection device, a first optical fiber, and a pair of tubes. The needle structure is configured to be inserted into an organic tissue, wherein the needle structure comprises a compartment. The dialysis membrane is configured to isolate the compartment from the organic tissue. The detection device comprises a detection portion and a plurality of receptors, wherein the plurality of receptors are disposed on an end surface of the detection portion for conjugating target antibodies, and the detection portion is disposed in the compartment. The first optical fiber is coupled to the needle structure and is configured to introduce light incident on photo-induced molecules adjacent to the end surface of the detection portion so as to cause a change in the pH level of the solution adjacent to the end surface of the detection portion. The pair of tubes is connected to the compartment and is configured to transport the solution containing the photo-induced molecules into the compartment.

According to another aspect of the present invention, a method of immunodetection comprises the steps of inserting a needle structure of an immunodetection probe into an organic tissue, wherein the needle structure comprises a compartment and a detection device, and the detection device comprises a detection portion and a plurality of receptors, wherein the plurality of receptors are disposed on an end surface of the detection portion for conjugating target antibodies, and the detection portion is disposed in the compartment; detecting the existence of the target antibodies conjugated with the receptors; transporting the solution containing the photo-induced molecules into the compartment; and introducing the light incident on the photo-induced molecules adjacent to the end surface of the detection portion so as to cause a change in the pH level of the solution adjacent to the end surface of the detection portion for dissociating the target molecule conjugated with the receptors.

BRIEF DESCRIPTION OF THE DRAWINGS

The objectives and advantages of the present invention will become apparent upon reading the following description and upon reference to the accompanying drawings in which.

DETAILED DESCRIPTION OF THE INVENTION

Figure 1:
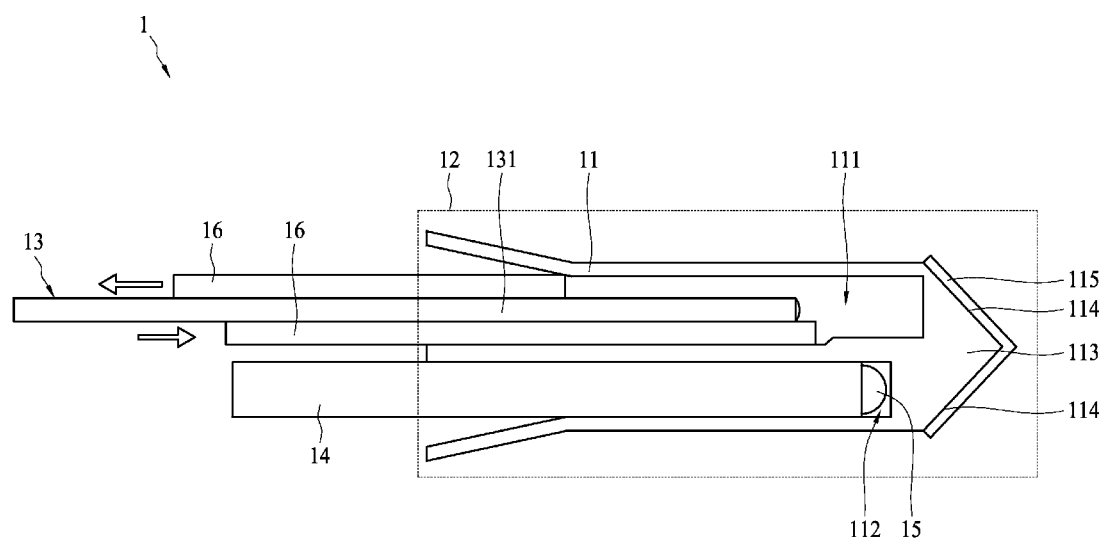
FIG. 1 is a diagram of a needle structure of an immunodetection probe according to one embodiment of the present invention.

FIG. 1 is a diagram of a needle structure of an immunodetection probe according to one embodiment of the present invention. The immunodetection probe 1 comprises a needle structure 11, a dialysis membrane 12, a detection device 13, an optical fiber 14, a lens 15, and a pair of tubes 16.

The needle structure 11 comprises a compartment 111 and a groove 112. The needle structure 11 is configured to be inserted into an organic tissue, thereby performing an in-situ detection. The compartment 111 and groove 112 can be, but are not limited to being, arranged in parallel. The compartment 111 can be a non-closed space. That is, the compartment 111 may have an opening for connecting to an external environment.

The dialysis membrane 12 is provided and is configured to isolate the compartment 111 from the organic tissue surrounding the needle structure 11. In this embodiment, the dialysis membrane 12 can contain the needle structure 11. In addition, the dialysis membrane 12 can be configured to cause target proteins to enter the compartment 111. Therefore, molecules above a specific volume are blocked, thus reducing the interference of the detection signals due to macromolecules.

The detection device 13 comprises a detection portion 131. The detection portion 131 is inserted into the compartment 111 for detecting target molecules diffusing in the compartment 111. The fiber 14 is connected to the needle structure 11 and is disposed in the groove 112 of the needle structure 11. The fiber 14 is configured to introduce light. The lens 15 is disposed on the optical path projected by the optical fiber 14. However, the disclosure should not be limited to the embodiment. The pair of tubes 16 is configured to conduct the compartment 111. One of the pair of tubes 16 can transport the solution into the compartment 111, while the other of the pair of tubes 16 can transport the solution out of the compartment 111. In this embodiment, the pair of tubes 16 is disposed on opposite sides of the detection portion 131 of the detection device 13.

Figure 2:
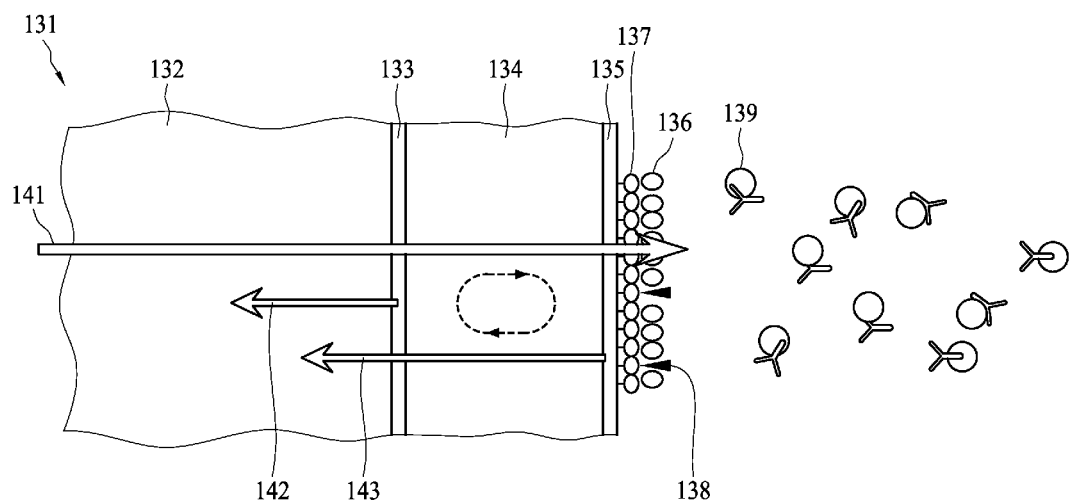
FIG. 2 is a diagram of the detection portion of the detection device according to one embodiment of the present invention.

FIG. 2 is a diagram of the detection portion 131 of the detection device 13 according to one embodiment of the present invention. The detection device 13 can be a fiber optic interferometer sensor. The detection portion 131 of the detection device 13 can comprise an optical fiber 132, a first reflective layer 133, an intermediate layer 134, a second reflective layer 135, and a plurality of receptors 136. The intermediate layer 134 serves as a resonant cavity of the detection device 13. The first and second reflective layers are disposed on opposite sides of the intermediate layer 134, wherein the first reflective layer 133 is disposed on an end surface of the fiber 132, the intermediate layer 134 is disposed on the first reflective layer 133, and the second reflective layer 135 is disposed on the intermediate layer 134. The receptors 136 are disposed on the outer side surface of the second reflective layer 135, i.e., an end surface of the detection portion 131. In this embodiment, the fiber 132 can be either a single mode fiber or a multimode fiber. The first and second reflective layers 133 and 135 can be a gold film with a thickness of 3 nm. The intermediate layer 134 can be a polymer layer which comprises poly-dimethylsiloxane (PDMS), wherein the length of the intermediate layer 134 can range from 10 μm to 50 μm. In one embodiment, the core diameter of the fiber 132 can be 17 μm, the diameter of the fiber can be 125 μm, the numerical aperture of the fiber can be 0.16, the incident wavelength of the fiber can be 1550 nm, and the length of the intermediate layer 134 can be 30 μm.

In addition, the receptor 136 can comprise an antibody, such as human cytochrome C. In particular, the end surface of the detection portion 131 can form thiol self-assembled monolayer (SAM) 137 first. After the thiol SAM 137 is activated, the human cytochrome C is immobilized. The end surface can be immersed in bovine serum albumin (BSA) solution 138 to eliminate any non-specific binding.

Referring to FIG. 1, the optical fiber 14 is optically coupled to the lens 15 so as to constrain irradiation range of the light from the optical fiber 14. In this embodiment, the lens 15 can be formed on the end surface of the fiber 14. The fiber can be a multimode fiber and the lens 15 can be a dip-formed SU8 lens. The focal length of the lens 15 can range from 0.5 mm to 10 mm, or 2.2 mm in a preferred embodiment. The diameter of the fiber 14 can be 200 μm. According to one embodiment of the present invention, a light spot with a 10 μm to 100 μm in diameter is formed on the end surface of the detection portion 131. According to another embodiment of the present invention, a light spot approximately 20 μm in diameter is formed on the end surface of the detection portion 131.

The needle structure 11 can integrate the detection device 13, the optical fiber 14, the lens 15, and the tubes 16 together to form the immunodetection probe 1. The needle structure 11 can cause the detection portion 131 of the detection device 13 and the tubes 16 to be immobilized toward a same direction. Moreover, the needle structure 11 can reflect the light of the optical fiber 14 and reverse the light toward the detection portion 131 of the detection device 13. In this embodiment, the needle structure 11 can have a needle shape. The needle structure 11 can comprise a tip portion 113, and the tip portion 113 can comprise two opposite inclined surfaces 114. The included angle between the inclined surfaces 114 can be, but is not limited to, 90 degrees. In particular, the needle structure 11 can be formed on a silicon substrate by using SU-8 photoresist, and the height of the needle structure 11 can be 300 μm. After completing the fabrication of the needle structure 11, a metal layer 115, such as a silver layer, is deposited on the inclined surfaces 114 by using e-beam evaporation to increase the reflection efficiency of the inclined surfaces 114.

Figure 3:
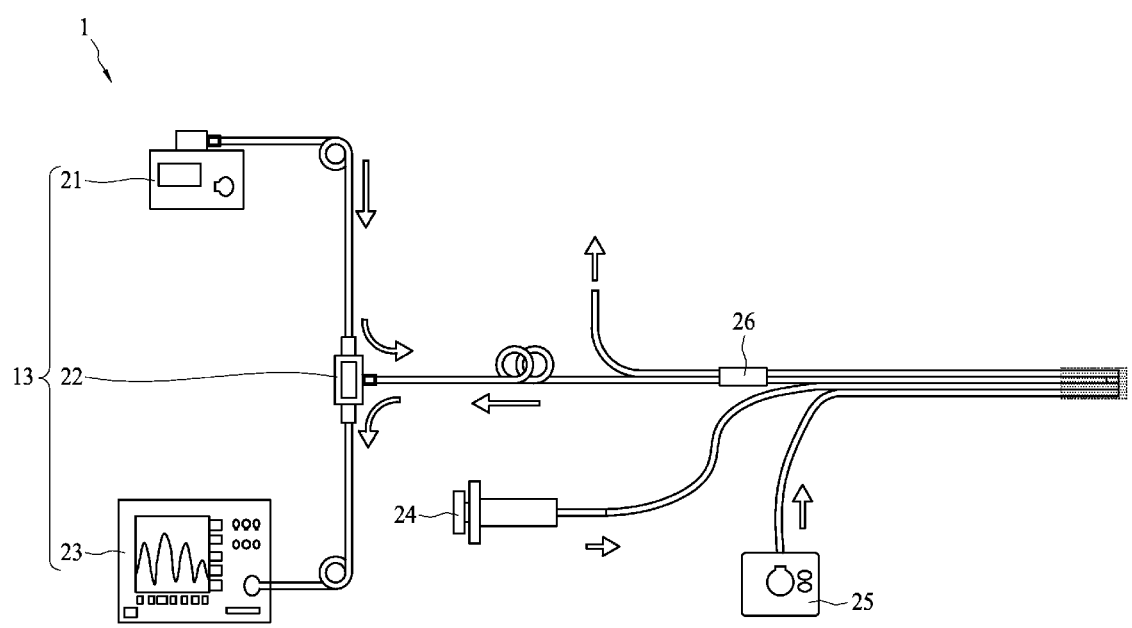
FIG. 3 is a diagram of a needle structure of an immunodetection probe according to one embodiment of the present invention.
Figure 4:
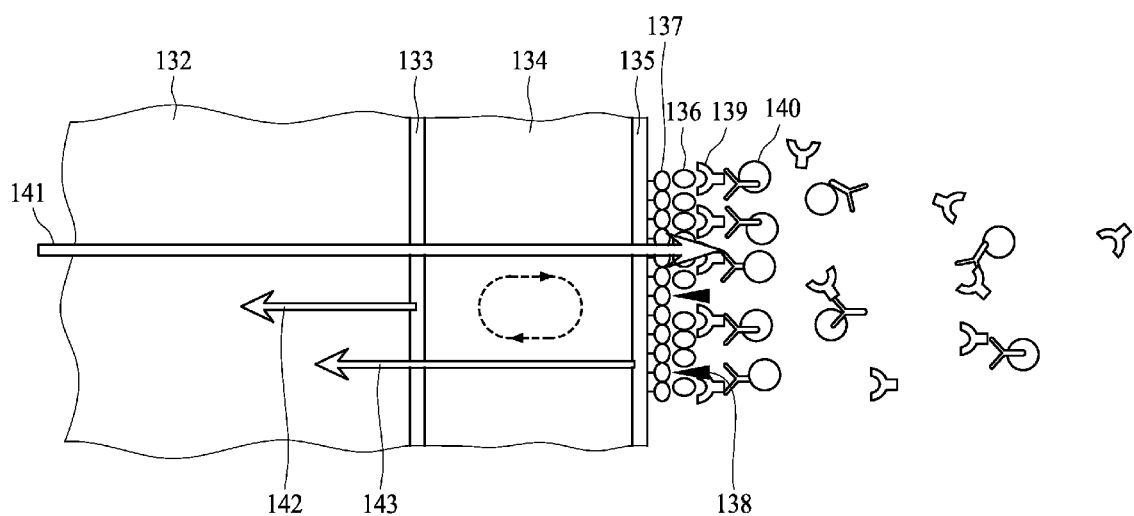
FIG. 4 is a diagram showing a conjugated condition of the receptor and the target molecule.
Figure 5:
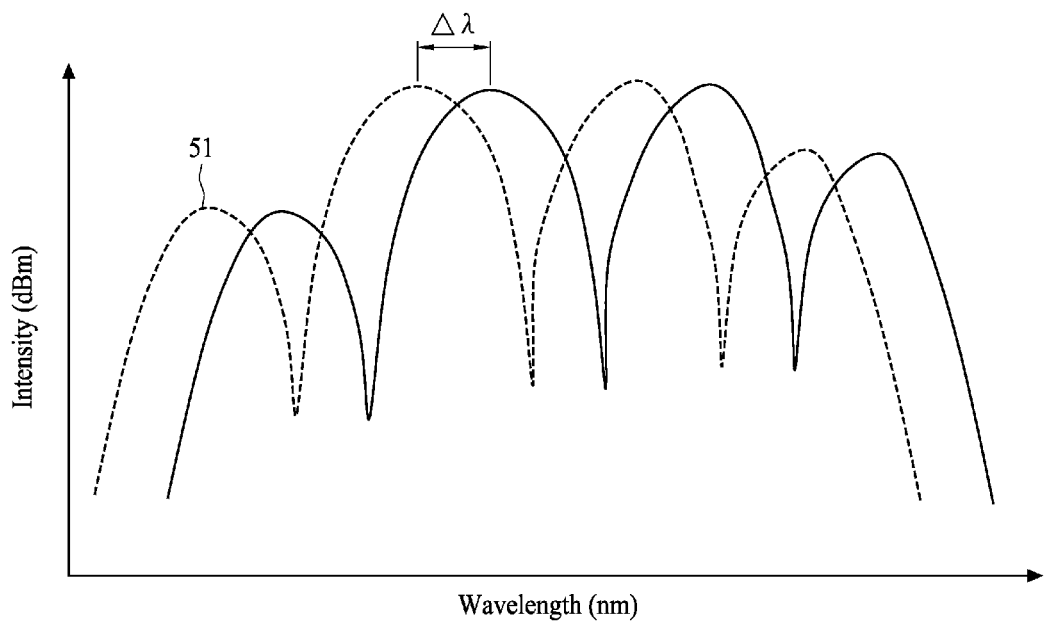
FIG. 5 is a diagram showing movement of an interference fringe generated by the detection device.

FIG. 3 is a diagram of a needle structure of an immunodetection probe 1 according to one embodiment of the present invention. Referring to FIGS. 1 and 3, the detection device 13 further comprises a light source generator 21, an optical circular 22, and an optical spectrum analyzer 23, wherein the light source generator 21, the detection portion 131, the optical circular 22, and the optical spectrum analyzer 23 are coupled to the optical circular 22 respectively. The detection device 13 detects the conjugation of the receptors 136 based on the optical interference principle. Referring to FIGS. 3 to 5, the light source generator 21 generates light 141, and the light 141 transmits into the detection portion 131 via a fiber camp splice 26. The first and second reflective layers 133 and 135 generate reflective light 142 and reflective light 143, respectively, when irradiated by the light 141. The reflective light 142 and 143 generate an interference fringe as shown in FIG. 5 after the interference. The wavelength of the reflective light 143 changes after the receptors 136 conjugate a target molecule 139, and thus the interference fringe 51 exhibits a shift Δλ in wavelength. Therefore, a conjugated condition of the receptor 136 and the target molecule 139 can be detected by observing the difference before the target molecule 139 conjugates the receptor 136 and after the target molecule 139 conjugates the receptor 136.

As shown in FIG. 4, when performing detection of the target molecule 139, a solution with a surface containing the gold nanoparticles labeled anti-rabbit IgG 140 is introduced into the compartment 111, whereby the gold nanoparticles labeled anti-rabbit IgG 140 and the target molecules 139 can be conjugated for amplifying a detection signal.

Figure 6:
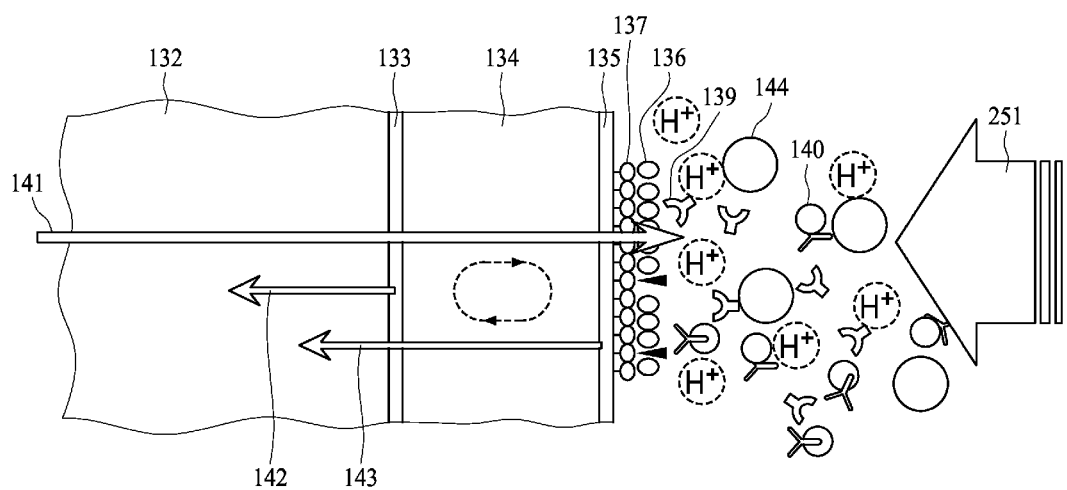
FIG. 6 is a reusable flow chart of the immunodetection probe according to one embodiment of the present invention.

FIG. 6 illustrates a reusable flow chart of the immunodetection probe 1 according to one embodiment of the present invention. Referring to FIGS. 1 and 3 again, the immunodetection probe 1 further comprises a solution injection device 24 and a light source 25. The solution injection device 24 can couple to one of the pair of the tubes 16 for providing a solution to the compartment 111. The light source 25 can couple to the optical fiber 14. After the detection is completed, the solution containing the photo-induced molecules 144 is injected into the compartment 111 via the solution injection device 24. Subsequently, the light source 25 is turned on to generate light 251. The light 251 is introduced into the needle structure 11 via the optical fiber 14, and the lens 15 constrains the emitting light 251 to a narrower irradiation range or focuses the light 251. The inclined surfaces 114 reflect the light 251 so that the light irradiates toward the end surface of the detection portion 131. The photo-induced molecules 144 in the optical path of the light 251 generated from the light source 25 react due to the light, and thus the pH level of the solution is altered. Once the pH level of the solution is altered, the link between the receptors 136 and the target molecule 139 dissociates, and the target molecule 139 dissociates. As a result, the receptor 136 can be reused for performing the detection. Since the light 251 is constrained or focused via the lens 15, the solution with the altered pH level is controlled within a smaller range, so that it will not diffuse out of the dialysis membrane 12.

In this embodiment, the light source 25 can provide ultraviolet light, and the photo-induced molecules 144 can comprise an o-Nitrobenzaldehyde (o-NBA) molecule. A proton can be released from an o-NBA molecule in nanoseconds when irradiated by ultraviolet light with a wavelength below 380 nm. In one embodiment, the pH level can rapidly decrease below 3.5 after 20 seconds under the ultraviolet light irradiation. Since the pH level of the solution is altered, the target molecule 139 and the receptors 136 conjugated by electrostatic force dissociate. The irradiation time of the light source 25 can be one to ten minutes in one embodiment, while the irradiation time of the light source 25 can be one to five minutes in another embodiment. In addition, the o-NBA molecules can be contained within poly(ethylene glycol) diacrylate (PEG), and the sizes of PEG-wrapped o-NBA particles range from 82 to 84 nm in diameter. Particles of this diameter can be readily confined by the dialysis membrane 12 and do not leak into the outside environment.

The present invention further discloses a method of immunodetection comprising the following steps. First, a needle structure 11 of an immunodetection probe 1 is inserted into an organic tissue, wherein the immunodetection probe 1 comprises a compartment 111 and a detection device 13. The detection device 13 comprises a detection portion 131 and a plurality of receptors 136, wherein the plurality of receptors 136 are disposed on an end surface of the detection portion 131 for conjugating target antibodies 139, and the detection portion 131 is disposed in the compartment 111. Subsequently, the existence of the target antibodies conjugated with the receptors 136 of the detection portion 131 is detected via the detection device 13. Subsequently, the solution containing the photo-induced molecules 144 is transported into the compartment 111. Lastly, light 251 is introduced via an optical fiber 14 to be incident on photo-induced molecules 144 adjacent to the end surface of the detection portion 131 so as to cause a change in the pH level of the solution adjacent to the end surface of the detection portion 131 for dissociating the target molecule conjugated with the receptors 136. The aforementioned method further comprises introducing a solution whose surface contains the gold nanoparticles labeled anti-rabbit IgG 140 into the compartment 111.

Accordingly, the present invention discloses an immunodetection probe comprising a needle structure. A transfusion pipe, a detection portion of a detection device, and an optical fiber are integrated into the needle structure. A receptor is disposed on a surface of the detection portion, wherein the receptor can detect proteins, enzymes, peptide, and so on. After the detection, the transfusion pipe can transport solution containing the photo-induced molecules into the needle structure. The optical fiber introduces light into the needle structure to irradiate the detection portion of the detection device for changing pH level of solution adjacent to the detection portion. Therefore, the proteins, enzymes, or peptide conjugated with the receptor dissociate and the receptor is reusable. Since the immunodetection probe according to one embodiment of the present invention combines a detection function and a reusable mechanism, continuous in-situ detection can be performed.

The above-described embodiments of the present invention are intended to be illustrative only. Numerous alternative embodiments may be devised by those skilled in the art without departing from the scope of the following claims.

What is claimed is:

1. An immunodetection probe, comprising:
a needle structure configured to be inserted into an organic tissue, wherein the needle structure comprises a compartment;
a dialysis membrane configured to isolate the compartment from the organic tissue;
a detection device comprising a detection portion and a plurality of receptors, wherein the plurality of receptors are disposed on an end surface of the detection portion for conjugating target antibodies, and the detection portion is disposed in the compartment;
a first optical fiber coupled to the needle structure and configured to introduce light incident on photo-induced molecules adjacent to the end surface of the detection portion so as to cause a change in the pH level of solution adjacent to the end surface of the detection portion; and
a pair of tubes connected to the compartment, wherein one of the pair of tubes is configured to transport solution containing the photo-induced molecules into the compartment and another of the pair of tubes is configured to transport the solution containing the photo-induced molecules out of the compartment.

2. The immunodetection probe of claim 1, further comprising a lens, wherein the lens is configured to constrain the irradiation range of the light from the first optical fiber, and the lens is disposed in the optical path of the light from the first optical fiber.

3. The immunodetection probe of claim 2, wherein the needle structure comprises a tip portion, and the tip portion comprises two opposite inclined surfaces, wherein the inclined surfaces are oppositely disposed on the end surface of the detection portion and disposed on an end surface of the first optical fiber, so as to reflect the light from the first fiber to the end surface of the detection portion.

4. The immunodetection probe of claim 3, wherein the lens is disposed on the end surface of the first optical fiber.

5. The immunodetection probe of claim 4, wherein the needle structure comprises a groove, the groove and the compartment are arranged in parallel, and the first optical fiber and the lens are disposed in the groove.

6. The immunodetection probe of claim 3, wherein the included angle between the opposite inclined surfaces of the tip portion is 90 degrees.

7. The immunodetection probe of claim 3, wherein the tip portion of the needle structure further comprises two metal layers, and the layers are respectively disposed on the inclined surfaces.

8. The immunodetection probe of claim 3, wherein the metal layers comprise silver.

9. The immunodetection probe of claim 1, wherein the detection portion of the detection device is disposed between the two tubes.

10. The immunodetection probe of claim 1, wherein the light comprises ultraviolet light.

11. The immunodetection probe of claim 1, wherein the receptor comprises an antibody.

12. The immunodetection probe of claim 1, wherein the photo-induced molecules comprise o-Nitrobenzaldehyde.

13. The immunodetection probe of claim 12, wherein the photo-induced molecules comprise PEG, and the o-Nitrobenzaldehyde molecules are contained within the PEG.

14. The immunodetection probe of claim 13, wherein the sizes of the photo-induced molecules range from 82 to 84 nm in diameter.

15. The immunodetection probe of claim 12, wherein the pH level is less than 3.5.

16. The immunodetection probe of claim 1, wherein the duration for which the light is incident on the photo-induced molecules adjacent to the end surface of the detection portion is one to ten minutes.

17. The immunodetection probe of claim 1, wherein the lens focuses the light adjacent to the end surface of the detection portion.

18. The immunodetection probe of claim 17, wherein the lens is configured to form a light spot 10 μm to 100 μm in diameter on the end surface of the detection portion.

19. The immunodetection probe of claim 17, wherein the focal length of the lens is 0.5 mm to 10 mm.

20. The immunodetection probe of claim 1, wherein the detection device is a fiber optic interferometer sensor.

21. The immunodetection probe of claim 1, wherein the first optical fiber is a single mode fiber or a multimode fiber.

22. The immunodetection probe of claim 1, wherein the detection portion comprises a second optical fiber, a first reflective layer, an intermediate layer, and a second reflective layer, the first and second reflective layers are disposed on opposite sides of the intermediate layer, and the first reflective layer is disposed on an end surface of the second optical fiber.

23. The immunodetection probe of claim 22, wherein the first and second reflective layers comprise gold.

24. The immunodetection probe of claim 22, wherein the intermediate layer comprises poly-dimethylsiloxane layer, and the length of the poly-dimethylsiloxane layer is 10 μm to 50 μm.

* * * * *